United States Patent [19]

Bonnemann et al.

[11] 4,006,149

[45] Feb. 1, 1977

[54] CATALYTIC PRODUCTION OF PYRIDINES FROM ALKYNES AND NITRILES

[75] Inventors: Helmut Bonnemann, Essen (Ruhr); Hartmut Schenkluhn, Mulheim (Ruhr), both of Germany

[73] Assignee: Studiengesellschaft Kohle M.b.H., Mulheim (Ruhr), Germany

[22] Filed: Apr. 2, 1975

[21] Appl. No.: 564,392

[30] Foreign Application Priority Data

Apr. 4, 1974 Germany .......................... 2416295

[52] U.S. Cl. .......................... 260/290 P; 260/294.9
[51] Int. Cl.[2] ........................................ C07D 213/08
[58] Field of Search ......... 260/294.9, 290 P, 290 R

[56] References Cited

UNITED STATES PATENTS 3,679,688  7/1972  Fenton .......................... 260/290 P

OTHER PUBLICATIONS

Wakatsuki et al., Tetrahedron Letters, No. 36, Pergamon Press, pp. 3383–3384, (1973).

*Primary Examiner*—Alan L. Rotman
*Attorney, Agent, or Firm*—Burgess, Dinklage & Sprung

[57] ABSTRACT

In the production of pyridines by the reaction of alkynes and nitriles in the presence of a cobalt-containing catalyst, special catalysts have been found to give high yields. The catalyst can be a cobalt-(I) complex compound of the type cyclooctenyl-cobalt(I)-cyclooctadiene, methyl heptadienyl-cobalt(I)-butadiene and cyclopentadienyl-cobalt(I)-cyclooctadiene, or it can be formed in situ by reducing a di- or tri-valent cobalt salt with zinc, cadmium, a metal of the main groups I to III of the Periodic Table or with an organometallic compound of any of the foregoing.

7 Claims, No Drawings

CATALYTIC PRODUCTION OF PYRIDINES FROM ALKYNES AND NITRILES

This invention relates to the catalytic production of pyridines from alkynes and nitriles and more particularly to a process for the selective cycloaddition of acetylene hydrocarbons and nitriles to form derivatives of pyridine by means of readily available cobalt catalysts.

It is known that alkynes can be cyclotrimerized over transition metal catalysts to form benzene derivatives (C.W. Bird in "Transition Metal Intermediates in Organic Synthesis", New York, London: Academic Press, 1967, pp. 1–29). In certain cases, nitriles can be included in the cyclization reaction resulting in substituted pyridines (H. Yamazaki and Y. Wakasuki, Tetrahedron Letters, 1973, p. 3383). A specific phosphane-containing complex compound of trivalent cobalt, a derivative of cyclopentadienyl-(triphenylphosphine)-cobaltatetraphenylcyclopentadiene, is used as the catalyst for the reaction. However, when using conventional cobalt salts, this compound can be obtained in very low yields only (about 10%) in a plurality of stages in difficult operations (see H. Yamazaki and N. Hagihara, J. Organometal. Chem., 21 (1970), p. 431). Therefore, the cost of production highly increases unavoidably when using the above-mentioned catalyst in a commercial pyridine synthesis. It is an object of this invention to provide a process for the production of the pyridine derivatives desired by means of a readily prepared catalyst having, moreover, low cost of production.

It has now been found surprisingly that the catalyst can be prepared in situ from readily available starting materials: Salts of inorganic or organic acids of divalent or trivalent cobalt are reacted with reducing agents in the presence of the alkynes and nitriles to be reacted, at least in one of these reactants, and, if necessary or desired, in additional extraneous solvents. Addition of further stabilizing components such as phosphanes or other electron donators is not necessary.

Examples of suitable cobalt compounds in anhydrous or hydrous form include $CoCl_2.6H_2O$, cobaltous carbonate, cobaltous hydroxide carbonate, cobaltous sulfate, cobaltous nitrate, cobaltous formate, cobaltous acetate, cobaltous acetyl acetonate, cobaltous ethylate, cobaltous t-butylate, cobaltous oxalate, cobaltous phenolate, cobaltous naphthenate and cobaltic acetyl acetonate.

Suitable reducing agents include metals of main groups I to III of the Periodic Table of Elements (Cotton/Wilkinson "Anorganische Chemie", 2nd edition, Weinheim, 1970) and zinc, cadmium as well as compounds of these metals containing at least one hydrogen attached to the element or an organic radical attached to the element through a carbon atom. In the presence of the monomers, the cobalt salts are converted without separation of metal into soluble complex compounds which generally are brown colored and in which the metal is present in a lower valency and which represent the catalyst proper.

The preformed organocobalt complex compounds in which the metal is already present in a lower valent state of bonding can also be used advantageously as catalysts for the cycloaddition. Preferably the known cyclooctenyl-cobalt-cyclooctadiene complexes, methylheptadienyl-cobalt-butadiene, and complexes of the cyclopentadienyl-cobalt-cyclooctadiene type have been found to be suitable complex compounds. All of these cobalt complexes can be prepared in high yields by the direct route.

Besides acetylene itself, monoalkyl and/or monoaryl-substituted derivatives but also disubstituted acetylenes such as butyne-(2), tolane or, for example, propargyl methyl ether may be used as suitable alkynes. It is also possible to carry out the reaction with two different acetylene derivatives as a cocycloaddition. For example, the joint reaction of acetylene, propyne and acetonitrile gives mixed lutidine derivatives in addition to alpha picoline and isomeric collidines. Examples of suitable nitrile components which may be used include alkyl, aryl and arylalkyl and alkenyl derivatives or dinitriles such as malonodinitrile or adipodinitrile as well as terphthalic acid dinitrile.

The process according to the invention is preferably carried out in the presence of an excess of nitrile (if necessary or desired in the presence of a diluent) at temperatures in the range between $-10°$ C. and $150°$ C. and preferably $50°$ to $100°$ C. under pressure conditions under which the reactants are completely or partially maintained in liquid state. In general, the pressures are not in excess of 30 atmospheres. The acetylenes charged are reacted substantially quantitatively. Excess nitrile can be recovered by distillation. Suitable diluents are paraffin hydrocarbons, aromatics, ethers, pure or water-containing alcohols and halohydrocarbons. It is not absolutely necessary for the course and progress of the reaction that the catalysts are prepared at low temperatures ($-40°$ C. to $-10°$ C.). It is also possible to introduce at, for example, $50°$ to $100°$ C. into a mixture of an acetylene, nitrile and either reducing agent or cobalt compound the residual component, i.e. the cobalt compound or reducing agent. Analogously the already reduced cobalt compounds may also be used. As has been stated above and will be illustrated in several examples, the catalyst, i.e., for example, the preformed organocobalt complex compounds, may be dissolved in the nitrile and the alkyne added to the solution.

Reducing agents which are spontaneously inflammable in the air such as alkyl aluminum compounds must be handled under a protective gas atmosphere. However, the use of a protective gas atmosphere is not necessary for the performance of the process of the invention itself.

The catalytic cycloaddition in accordance with the invention is carried out with particular advantage, i.e. particularly high yields, as a one-shot reaction.

The pyridine derivatives prepared by this process are useful starting materials for pharmaceutical industry for the production of, for example, disinfectants or insecticides. They are also used as auxiliary materials in the synthesis of polymers and a vulcanization accelerators. Pyridine derivatives having unsaturated substituents are of great importance as monomers in plastics industry (dimethyl vinyl pyridine).

EXAMPLE 1

A solution of 1.8 g. ( 8 mmoles) of methylheptadienyl-cobalt-butadiene in 40 ml toluene is mixed with 20 g. (0.5 moles) of liquid propyne and 41 g. (1 mole) of acetonitrile at a temperature below $-40°$ C. The brown-colored solution is sucked at $-30°$ C. into an evacuated and precooled 500 ml stainless steel autoclave and heated within 30 minutes to $+80\pm5°$ C. within 30 minutes while shaking. This temperature is maintained constant for 4 hours. During this time, the pressure drops from 7 atmospheres to 1 atmosphere. After having cooled the reaction vessel (no residual pressure), the reaction mixture is separated by distillation.

| Fraction 1: | boiling range 75–110° C./760 toor (recovered acetonitrile and solvent) | 68.8 g. |
|---|---|---|
| Fraction 2: | boiling range 46–65° C./11 torr (pyridines and carbocyclic by-products) | 24.9 g. |
| Residue: | 3.2 g. | |

A sample of fractions 1 and 2 was analyzed by gas chromatography.

| Capillary column: | FFAP |
|---|---|
| Carrier gas: | Helium |
| Detector: | FID |

Yield (based on alkyne reacted):

| 13.0 g. | 2,4,6-collidine | | (43%) |
|---|---|---|---|
| 5.7 g. | 2,3,6-collidine | | (19%) |
| | | Total | (62%) |
| 3.8 g. | pseudo cumene | | |
| 2.4 g. | mesitylene | | |

EXAMPLE 2

The procedure of Example 1 is repeated except that acetylene is subsequently introduced at −30° C under pressure as alkyne component into the mixture contained in the pressure vessel.
Charged:
2.7 g. (12.0 mmoles) methyl heptadienyl-cobalt-butadiene in 40 ml. toluene
49.2 g. (1.2 moles) acetonitrile
15.6 g. (0.6 moles) acetylene
The reaction mixture is separated by distillation.

| Fraction 1: | Boiling range 78–111° C./760 toor (recovered acetonitrile, benzene, and solvent) | 77.6 g. |
|---|---|---|
| Fraction 2: | Boiling point (alpha picoline) | 20.6 g. |
| Residue: | 3.2 g. | |
| Yield: | 20.6 g. alpha picoline | (74%) |
| | 3.3 g. benzene | |

EXAMPLE 3

The procedure of Example 1 is followed except that π-cyclooctenyl-cobalt-cyclooctadiene is used in place of methylheptadienyl-cobalt-butadiene and propionitrile is used in place of acetonitrile.
Charged:
3.0 g. (11 mmoles) π-cyclooctenyl-cobalt-cyclooctadiene in 45 ml. toluene
60.5 g. (1.1 moles) propionitrile
22.0 g. (0.55 moles) propyne
The reaction mixture is separated by distillation.

| Fraction 1: | Boiling range 98–111° C./760 toor (recovered propionitrile and solvent) | 89.7 g. |
|---|---|---|
| Fraction 2: | Boiling range 47–72° C./12 torr (pyridines and carbocyclic by-products) | 29.6 g. |
| Residue: | 4.1 g. | |
| Yield: | 16.7 g. 2-ethyl-4,6-dimethyl-pyridine | (45%) |
| | 6.3 g. 2-ethyl-3,6-dimethyl-pyridine | (17%) |
| | Total | (62%) |
| | 3.5 g. pseudocumene | |
| | 3.1 g. mesitylene | |

EXAMPLE 4

The procedure of Example 3 is followed except that aqueous ethyl alcohol is used as the solvent in place of toluene.
Charged:
2.2 g. (8 mmoles) π-cyclooctenyl-cobalt-cyclooctadiene in 50 ml. 60% aqueous ethyl alcohol
46.2 g. (0.84 moles) propionitrile
16.8 g. (0.42 moles) propyne
The reaction mixture withdrawn is taken up in 200 ml ice water and processed by acid-base separation. After extraction with diethyl ether and separation of the readily volatile components (b.p., ≧96° C./760 torr), the pyridines are obtained in the boiling range of 69° to 74° C./13 torr.

| Yield: | 11.6 g. 2-ethyl-4,6-dimethyl-pyridine | (41%) |
|---|---|---|
| | 4.3 g. 2-ethyl-3,6-dimethyl-pyridine | (15%) |
| | Total | (56%) |

EXAMPLE 5

The procedure of Example 1 is followed except that cyclopentadienyl-cobalt-cyclooctadiene is used in place of methyl heptadienyl-cobalt-butadiene.
Charged:
2.3 g. (10 mmoles) cyclopentadienyl-cobalt-cyclooctadiene in 40 ml. toluene
41 g. (1 mole) acetonitrile
20 g. (0.5 moles) propyne
The reaction mixture is separated by distillation.

| Fraction 1: | Boiling range 78–111° C./760 torr (recovered acetonitrile and solvent) | 68.0 g. |
|---|---|---|
| Fraction 2: | Boiling range 48–68° C./12 torr (pyridines and carbocyclic by-products) | 24.6 g. |
| Residue: | 4.3 g. | |
| Yield: | 12.4 g. 2,4,6-collidine | (41%) |
| | 9.0 g. 2,3,6-collidine | (30%) |
| | Total | (71%) |
| | 2.2 g. pseudocumene | |
| | 1.0 g. mesitylene | |

EXAMPLE 6

To a solution of 1.4 g. (6 mmoles) σ-cyclooctenyl-cobalt-cyclooctadiene in 30 ml. toluene is added dropwise at −10° C. within 30 minutes a mixture of 33 g. (0.6 moles) of propionitrile and 30.6 g. (0.3 moles) of phenylacetylene. After stirring for 6 hours at −10° to ± 0° C., the reaction mixture is separated by distillation.

| Fraction 1: | Boiling range 95–112° C./760 torr (recovered propionitrile and solvent) | 56.4 g. |
|---|---|---|

-continued

| Fraction 2: | Boiling point 143° C./760 torr (phenyl acetylene) | 13.5 g. |
| --- | --- | --- |
| Fraction 3: | Boiling range 180–210° C./10⁻¹ torr (pyridines) | 10.5 g. |
| Residue: | 9.2 g. (triphenyl benzene and catalyst components) | |
| Yield: | 7.0 g. 2,4-diphenyl-6-ethyl pyridine | (32%) |
| | 3.5 g. 2,5-diphenyl-6-ethyl pyridine | (16%) |
| | Total | (48%) |

EXAMPLE 7

A mixture of 2.4 g. (10 mmoles) cobaltous chloride.$6H_2O$ 41 g. (1 mole) acetonitrile and 20 g. (0.5 moles) of liquid propyne is mixed at a temperature below −40° C. with 0.8 g. (20 mmoles) of sodium boranate. After warming to −20° C., the solution turns from blue to deep brown. It is sucked into an evacuated and precooled 500 ml. stainless steel autoclave, reacted as described in Example 1 and separated by distillation.

| Yield: | 14.8 g. 2,4,6-collidine | | (49%) |
| --- | --- | --- | --- |
| | 6.3 g. 2,3,6-collidine | | (21%) |
| | | Total | (70%) |
| | 3.2 g. pseudocumene | | |
| | 1.6 g. mesitylene | | |

EXAMPLE 8

The procedure of Example 7 is followed except that anhydrous cobaltous chloride is used and benzonitrile is substituted for acetonitrile.
Charged:
 1.6 g. (12 mmoles) cobaltous chloride
 0.9 g. (24 mmoles) sodium boranate
 144.2 g. (1.4 moles) benzonitrile
 28.0 g. (0.7 moles) propyne
Distillation gives

| Fraction 1: | Boiling range 51–90° C./13 torr (carbocyclic by-products and recovered benzonitrile) | 133.1 g. |
| --- | --- | --- |
| Fraction 2: | Boiling range 85–95° C./10⁻¹ torr (pyridines) | 34.6 g. |
| Residue: | 4.5 g. | |
| Yield: | 23.7 g. 2-phenyl-4,6-dimethyl pyridine | (37%) |
| | 10.9 g. 2-phenyl-3,6-dimethyl pyridine | (17%) |
| Total | (54%) | |
| | 5.3 g. pseudocumene | |
| | 4.2 g. mesitylene | |

EXAMPLE 9

The procedure of Example 7 was followed except that anhydrous cobaltous chloride is used and benzyl cyanide is substituted for acetonitrile
Charged:
 0.65 g. (5 mmoles) cobaltous chloride
 0.38 g. (10 mmoles) sodium boranate
 58.5 g. (0.5 moles) benzyl cyanide
 10.0 g. (0.25 moles) propyne
The reaction mixture is separated by distillation.

| Fraction 1: | Boiling range 48–60° C./13 torr (carbocyclic by-products) | 3.2 g. |
| --- | --- | --- |
| Fraction 2: | Boiling point 63° C./10⁻¹ torr (recovered benzyl cyanide) | 49.0 g. |
| Fraction 3: | Boiling range 91–100° C./10⁻¹ torr (pyridines) | 14.3 g. |
| Residue: | 2.1 g. | |

-continued

| Yield: | 9.4 g. 2-benzyl-4,6-dimethyl pyridine | (38%) |
| --- | --- | --- |
| | 4.9 g. 2-benzyl-3,6-dimethyl pyridine | (20%) |
| | Total | (58%) |
| | 1.8 g. pseudocumene | |
| | 1.4 g. mesitylene | |

EXAMPLE 10

The procedure of Example 7 is followed except that cobaltous formate is used in place of cobaltous chloride.$6H_2O$ and the reaction is carried out at 100° C.
Charged:
 1.2 g. (8 mmoles) cobaltous formate
 0.6 g. (16 mmoles) sodium boranate
 41.0 g. (1 mole) acetonitrile
 20.0 g. (0.5 moles) propyne
Distillation by the procedure of Example 1 gives:

| Yield: | 14.8 g. 2,4,6-collidine | | (49%) |
| --- | --- | --- | --- |
| | 6.0 g. 2,3,6-collidine | | uz,25/30 (20%) |
| | | Total | (69%) |
| | 2.8 g. pseudocumene | | |
| | 1.2 g. mesitylene | | |

EXAMPLE 11

The procedure of Example 7 is followed except that cobaltous acetate is used in place of cobaltous chloride-$6H_2O$ and propionitrile is substituted for acetonitrile.
Charged
 1.1 g. (6 mmoles) cobaltous acetate
 0.46 g. (12 mmoles) sodium boranate
 44.0 g. (0.8 moles) propionitrile
 16.0 g. (0.4 moles) propyne
Distillation as in Example 3 gives:

| Yield: | 11.1 g. 2-ethyl-4,6-dimethyl pyridine | | (41%) |
| --- | --- | --- | --- |
| | 5.9 g. 2-ethyl-3,6-dimethyl pyridine | | (22%) |
| | | Total | (63%) |
| | 2.6 g. pseudocumene | | |
| | 2.3 g. mesitylene | | |

EXAMPLE 12

The procedure of Example 7 is followed except that cobaltous acetyl acetonate is used in place of cobaltous chloride.$6H_2O$ and propionitrile is substituted for acetonitrile.
Charged:
 2.1 g. (8 mmoles) cobaltous acetyl acetonate
 0.6 g. (16 mmoles) sodium boranate
 55.0 g. (1 mole) propionitrile
 20.0 g. (0.5 moles) propyne Distillation by the procedure of Example 3 gives:

| Yield: | 16.2 g. 2-ethyl-4,6-dimethyl pyridine | (48%) |
| --- | --- | --- |
| | 7.4 g. 2-ethyl-3,6-dimethyl pyridine | (22%) |
| | Total | (70%) |
| | 3.6 g. pseudocumene | |
| | 2.2 g. mesitylene | |
| | based on acetylene reacted | |

EXAMPLE 13

A mixture of 0.4 g. (3 mmoles) cobaltous chloride 6 g. (0.15 moles) of liquid propyne and 20 ml of diethyl ether is mixed at a temperature below −40° C. with 0.5 g. (6 mmoles) of ethyl magnesium chloride in 8 ml diethyl ether. After stirring for 30 minutes (color change from blue to deep brown), 16.5 g. (0.3 moles) of propionitrile are added and the mixture is sucked into an evacuated and precooled 100 ml stainless steel autoclave. The mixture is heated for 5 hours at 70±5° C. while shaking. After cooling, it is separated by distillation by the procedure of Example 3.

| Yield: | 4.0 g. 2-ethyl-4,6-dimethyl pyridine | (39%) |
| --- | --- | --- |
| | 3.0 g. 2-ethyl-3,6-dimethyl pyridine | (29%) |
| | Total | (68%) |
| | 0.8 g. pseudocumene | |
| | 0.7 g. mesitylene | |

EXAMPLE 14

The procedure of Example 7 is followed except that anhydrous cobaltous chloride is used and n-butyl lithium dissolved in pentane is substituted for sodium boranate.

Charged:
  0.5 g. (4 mmoles) cobaltous chloride
  0.5 g. (8 mmoles) n-butyl lithium in 10 ml. pentane
  29.7 g. (0.54 moles) propionitrile
  10.8 g. (0.27 moles) propyne Distillation by the procedure of Example 3 gives:

| Yield: | 8.4 g. 2-ethyl-4,6-dimethyl pyridine | (46%) |
| --- | --- | --- |
| | 4.6 g. 2-ethyl-3,6-dimethyl pyridine | (25%) |
| | Total | (71%) |
| | 1.4 g. pseudocumene | |
| | 1.0 g mesitylene | |

EXAMPLE 15

A suspension of 0.5 g. (3.8 mmoles) of cobaltous chloride in 15.4 g. (0.16 moles) heptyne-1 is mixed at 20° C. with a solution of 0.3 g. (7.9 mmoles) of sodium boranate in 16.4 g. (0.4 moles) acetonitrile and heated for 4 hours at 80° C. The brown colored reaction solution is subjected to fractional distillation.

| Fraction 1: | Boiling range 80–100° C./760 torr (recovered acetonitrile and heptyne-1) | 19.3 g |
| --- | --- | --- |
| Fraction 2: | Boiling range 84;14 96° C./10⁻⁴ torr (pyridines) | 7.0 g. |
| Residue: | 3.9 g. (carbocyclic by-products and catalyst components) | |
| Yield: | 4.6 g. 2,4-di-(n)pentyl-6-methyl pyridine | (38%) |
| | 2.4 g. 2,5-di(n)pentyl-6-methyl pyridine | (20%) |
| | Total | (58%) |

EXAMPLE 16

The procedure of Example 15 is followed except that phenyl acetylene is used in place of heptyne-1, caprylonitrile is used in place of acetonitrile and toluene is used as the solvent.

Charged:
  0.4 g. (3 mmoles) cobaltous chloride
  0.27 g. (7 mmoles) sodium boranate
  25 g. (0.2 moles) caprylonitrile
  10.2 g. (0.1 moles) phenyl acetylene
  30 ml toluene The reaction mixture is separated by distillation.

| Fraction 1: | Boiling range 110–140° C./760 torr (solvent and recovered phenyl acetylene) | 30.4 g. |
| --- | --- | --- |
| Fraction 2: | Boiling range 83° C./12 torr (recovered caprylonitrile) | 22.3 g. |

The residue (8.5 g.) is dissolved in 40 ml. benzene and subjected to chromatography on alumina. From the eluates are recovered

| 4.1 g. 2,4-diphenyl-6-heptyl pyridine | (38%) |
| --- | --- |
| 2.1 g. 2,5-diphenyl-6-heptyl pyridine | (19%) |
| Total | (57%) |

EXAMPLE 17

The procedure of Example 15 is followed except that phenyl acetylene is used in place of heptyne-1 and chlorobenzene is used as the solvent.

The reaction mixture is separated by distillation.

Charged:
  1.1 g. (8.5 mmoles) cobaltous chloride 0.65 g. (17 mmoles) sodium boranate 41.0 g. (1 mole) acetonitrile 51.0 g. (0.5 moles) phenyl acetylene 60 ml. chlorobenzene

| Fraction 1: | Boiling point 82° C./760 torr (recovered acetonitrile) | 33.0 g. |
| --- | --- | --- |
| Fraction 2: | Boiling range 130–145° C./760 torr (solvent and recovered phenyl acetylene) | 89.6 g. |
| Fraction 3: | Boiling range 170–190° C./10⁻⁴ torr (pyridines) | 22.8 g. |
| Residue: | 20.4 g. (triphenyl benzene and catalyst components) | |
| Yield: | 17.9 g. 2,4-diphenyl-6-methyl pyridine | (40%) |
| | 4.9 g. 2,4-diphenyl-6-methyl pyridine | (11%) |
| | Total | (51%) |

EXAMPLE 18

A mixture of 0.6 g. (4.6 mmoles) of cobaltous chloride, 30 ml tetrahydrofurance and 25.5 g. (0.25 moles) phenyl acetylene is mixed at ±0° C. with 0.2 g (5 mmoles) lithium alanate. Within 20 minutes the solution changes its color from blue to deep brown with spontaneous heating to 42° C. After addition of 27.5 g. (0.5 moles) propionitrile, the mixture is heated for 6 hours at 65° C., cooled and separated by distillation by the procedure of Example 5.

| Yield: | 6.7 g. 2,4-diphenyl-6-ethyl pyridine | (38%) |
|---|---|---|
| | 3.0 g. 2,5-diphenyl-6-ethyl pyridine | (17%) |
| | Total | (55%) |

EXAMPLE 19

To a mixture of 0.65 g. (5 mmoles) cobaltous chloride, 30 ml. tetrahydrofurane, 27.5 g. (0.5 moles) propionitrile and 25.5 g. (0.25 moles) phenyl acetylene is added 0.1 g (12.5 mmoles) lithium hydride and the mixture is refluxed for 7 hours. The reaction mixture is separated by the procedure of Example 5.

| Yield: | 4.1 g. 2,4-diphenyl-6-ethyl pyridine | (32%) |
|---|---|---|
| | 2.3 g. 2,5-diphenyl-6-ethyl pyridine | (18%) |
| | Total | (50%) |

EXAMPLE 20

A mixture of 1.3 g. (10 mmoles) cobaltous chloride, 40 ml. tetrahydrofuran and 41 g. (1 mole) acetonitrile is mixed with 0.15 g. (21 mmoles) lithium and heated for 30 minutes at 60° C. After addition of 51 g. (0.5 moles) phenyl acetylene, the mixture is heated for 5 hours at 85° C. and separated by distillation by the procedure of Example 15.

| Yield: | 12.6 g. 2,4-diphenyl-6-methyl pyridine | (31%) |
|---|---|---|
| | 7.4 g. 2,5-diphenyl-6-methyl pyridine | (18%) |
| | Total | (49%) |

EXAMPLE 21

0.25 Grams (11 mmoles) of finely divided sodium are added at ±0° C. to a mixture of 0.7 g. (5.4 mmoles) cobaltous chloride, 30 ml tetrahydrofuran and 25.5 g. (0.25 moles) phenyl acetylene and the mixture is heated for 15 minutes to 45° C. Thereafter the dark brown solution is mixed with 27.5 g. (0.5 moles) propionitrile, refluxed for 5 hours, cooled and separated by distillation as in Example 5.

| Yield: | 4.0 g. 2,4-diphenyl-6-ethyl pyridine | (34%) |
|---|---|---|
| | 2.0 g. 2,5-diphenyl-6-ethyl pyridine | (17%) |
| | Total | (51%) |

EXAMPLE 22

The procedure of Example 19 is followed except that acetonitrile is used in place of propionitrile and magnesium activated with iodine is used in place of lithium hydride.

Charged:
 0.65 g. (5 mmoles) cobaltous chloride in 30 ml. tetrahydrofuran
 0.24 g. (10 mmoles) magnesium
 18.9 g. (0.46 moles) acetonitrile
 23.5 g. (0.23 moles) phenyl acetylene The reaction mixture is distilled as in Example 15.

| Yield: | 9.9 g. 2,4-diphenyl-6-methyl pyridine | (44%) |
|---|---|---|
| | 4.1 g. 2,5-diphenyl-6-methyl pyridine | (18%) |
| | Total | (62%) |

EXAMPLE 23

To a mixture of 1.3 g. (5 mmoles) cobaltous acetyl acetonate, 27.5 g. (0.5 moles) propionitrile and 25.5 g. (0.25 moles) phenyl acetylene is added dropwise at 22° C. within 10 minutes a solution of 1.4 g. (11 mmoles) diethyl ethoxyaluminum in 20 ml. toluene. After heating for 4 hours at 85° C. the mixture is separated by distillation as in Example 5.

| Yield: | 7.9 g. 2,4-diphenyl-6-ethyl pyridine | (36%) |
|---|---|---|
| | 4.2 g. 2,5-diphenyl-6-ethyl pyridine | (19%) |
| | Total | (55%) |

EXAMPLE 24

The procedure of Example 23 is followed except that zinc diethyl is added dropwise at 0° C. in place of diethylethoxyaluminum.

Charged:
 1.3 g. (5 mmoles) cobaltous acetyl acetonate
 0.6 g. (5mmoles) zinc diethyl in 20 ml toluene
 27.5 g. (0.5 moles) propionitrile
 25.5 g. (0.25 moles) phenyl acetylene

| Yield: | 5.9 g. 2,4-diphenyl-6-ethyl pyridine | (35%) |
|---|---|---|
| | 2.4 g. 2,5-diphenyl-6-ethyl pyridine | (14%) |
| | Total | (49%) |

EXAMPLE 25

A mixture of 20.6 g. (0.2 moles) benzonitrile and 10.2 g. (0.1 mole) phenyl acetylene is added at 20° C. to a solution of 2.1 g. (6 mmoles) cobaltic acetyl acetonate in 20 ml tetrahydrofuran. After addition of 0.44 g. (18 mmoles) iodine-activated magnesium, the mixture is heated for 10 hours at 65° C. and separated by distillation.

| Fraction 1: | Boiling point 66° C/760 torr (solvent) | 17.6 g. |
|---|---|---|
| Fraction 2: | Boiling point 143° C./760 torr (recovered phenyl acetylene) | 3.5 g. |
| Fraction 3: | Boiling point 83° C./15 torr (recovered benzonitrile) | 18.7 g. |

The residue (9.8 g.) is dissolved in 50 ml benzene and subjected to chromatography on alumina. From the eluates are recovered

| | |
|---|---|
| 3.8 g. 2,4,6-triphenyl pyridine | (38%) |
| 1.3 g. 2,3,6-triphenyl pyridine | (13%) |
| Total | (51%) |
| 2.6 g. triphenyl benzene (2 isomers) | |

EXAMPLE 26

The procedure of Example 23 is followed except that cobaltic acetyl acetonate is used in place of cobaltous acetyl acetonate and triethyl aluminum is used in place of diethyl ethoxyaluminum.
Charged:
  1.8 g. (5 mmoles) cobaltic acetyl acetonate
  1.8 g. (16 mmoles) triethyl aluminum in 20 ml. toluene
  27.5 g. (0.5 moles) propionitrile
  25.5 g. (0.25 moles) phenyl acetylene
The reaction mixture is separated by distillation as in Example 5.

| | | | |
|---|---|---|---|
| Yield: | 5.6 g. 2,4-diphenyl-6-ethyl pyridine | | (36%) |
| | 3.3 g. 2,5-diphenyl-6-ethyl pyridine | | (21%) |
| | | Total | (57%) |

EXAMPLE 27

To a mixture of 1.8 g. (5 mmoles) cobaltic acetyl acetonate, 30 ml toluene and 25.5 g. (0.25 moles) phenyl acetylene is added dropwise at 22° C. within 5 minutes a solution of 1.7 g. (7.7 mmoles) ethyl aluminum sesquichloride in 5 ml. toluene. After heating to 50° C. for a short period of time, a brown colored solution is obtained. 1.7 Grams (17 mmoles) triethylamine are added to complex the Lewis acids. Thereafter 27.7 g. (0.5 moles) propionitrile are rapidly added dropwise. After heating for 3 hours at 85° C., the mixture is separated by distillation as in Example 5.

| | | | |
|---|---|---|---|
| Yield: | 6.3 g. 2,4-diphenyl-6-ethyl pyridine | | (27%) |
| | 4.4 g. 2,5-diphenyl-6-ethyl pyridine | | (19%) |
| | | Total | (46%) |

EXAMPLE 28

A solution of 1.8 g. (8 mmoles) methyl heptadienyl-cobalt-butadiene in 30 ml pentane is mixed at a temperature below −40° C. with 10 g. (0.25 moles) of liquid propyne and 41 g. (1 mole) acetonitrile. After having sucked the brown colored solution at −30° C. into an evacuated and precooled 500 ml stainless steel autoclave, 6.5 g. (0.25 moles) acetylene are introduced under pressure and the autoclave is heated to 80° C. ± 5° C. within 45 minutes while shaking. This temperature is maintained constant. In doing so, the pressure drops from 10 to 1.5 atmospheres. After cooling of the reaction vessel (no residual pressure), the reaction mixture is separated by distillation giving the following products:

| Product | Grams | Yield, % |
|---|---|---|
| α-picoline | 3.9 | 16.9 |
| 2,3-lutidine | 0.6 | 2.3 |
| 2,4-lutidine | 2.2 | 8.3 |
| 2,6-lutidine | 5.9 | 21.9 |
| 2,3,6-collidine | 2.0 | 6.6 |
| 2,4,6-collidine | | 12.9 |
| benzene | 0.3 | |
| toluene | 0.7 | |
| xylenes (o, m, p) | 0.9 | |
| trimethyl benzenes (1,3,5; 1,2,4) | 0.3 | |

EXAMPLE 29

3.3 Grams (15 mmoles) methyl heptadienyl-cobalt-butadiene are dissolved in 50 ml. toluene. The solution is mixed at −40° C. with 4.1 g. (75 mmoles) of liquid butyne and 8.3 g. (150 mmoles) propionitrile. The mixture is introduced by suction at −20° C. into an evacuated and precooled 250 ml stainless steel autoclave. The temperature is raised within 20 minutes to 85° ± 5° C. while shaking and maintained constant for 6 hours. During this time, the pressure drops from 4 to 0.5 atmospheres. After cooling (no residual pressure), the mixture is separated by distillation.

| | | |
|---|---|---|
| Fraction 1: | Boiling range 96–110° C./760 torr (recovered propionitrile and solvent) | 49.7 g. |
| Fraction 2: | Boiling range 51–63° C./10⁻² toor (pyridine and carbocyclic by-product) | 5.0 g. |
| Residue: | 3.7 g. | |
| Yield: | 4.2 g. 2-ethyl-3,4,5,6-tetramethylpyridine (69%) | |
| | 0.8 g. hexamethyl benzene | |

EXAMPLE 30

The procedure of Example 1 is followed except that freshly distilled acrylonitrile is used in place of acetonitrile and pentane is used as the solvent.
After the mixture has been introduced into the pressure vessel by suction, shaking is started. In doing so, the temperature increases autothermally to 58° C. within 20 minutes. This temperature is maintained constant for 4 hours by heating. During this time, the pressure drops from 5 to 0.7 atmospheres. After cooling, the reaction mixture is mixed with 100 mg. of 4-t-butyl pyrocatechol as polymerization inhibitor and all volatile components are removed by condensation under high vacuum.
Charged:
  2.2 g. (10 mmoles) methyl heptadienyl-cobaltbutadiene in 50 ml pentane 53 g. (1 mole) acrylonitrile
  20 g. (0.5 moles) propyne

| | | |
|---|---|---|
| Fraction 1: | Temperature of the bath,=>70° C./10⁻¹ torr | 75.2 g. |
| Residue: | 30.8 g. of a highly viscous mass (polymers and catalyst components) | |

Fraction 1 is again mixed with 100 mg. 4-t-butyl-pyrocatechol and redistilled.

| | | |
|---|---|---|
| Fraction 2: | Boiling point, <20° C./14 torr (recovered acrylonitrile and solvent) | 47.7 g. |
| Fraction 3: | Boiling range 49–58° C./14 torr (carbocyclic by-products) | 7.3 g. |
| Fraction 4: | Boiling range 81–86° C./14 torr (pyridine derivative) | 17.9 g. |
| Residue: | 1.9 g. | |

-continued

| Yield: | 17.9 g. 2-vinyl-dimethyl pyridine (54%) |
| --- | --- |
| | 4.3 g. pseudocumene |
| | 3.0 g. mesitylene |

EXAMPLE 31

To a mixture of 0.5 g. (2.3 mmoles) methyl heptadienyl-cobalt-butadiene, 12.8 g. (0.1 mole) terephthalic acid dinitrile and 150 ml toluene are added dropwise at −30° C. within 10 minutes 10.2 g. (0.1 mole) phenyl acetylene and the mixture is heated for 24 hours at 85° C. After cooling, the solvent and unreacted phenyl acetylene are distilled off under vacuum. The glassy residue (18.3 g.) is taken up in 80 ml. hot benzene and subjected to chromatography on alumina. From the eluates are recovered:

| 3.1 g. of 1 | (35%) |
| --- | --- |
| 0.5 g. of 2 | ( 7%) |

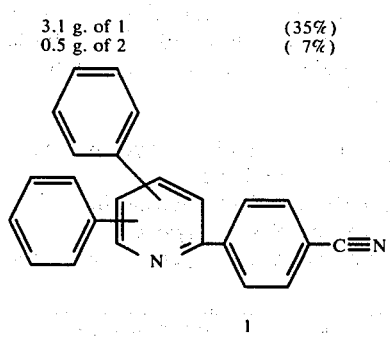

1

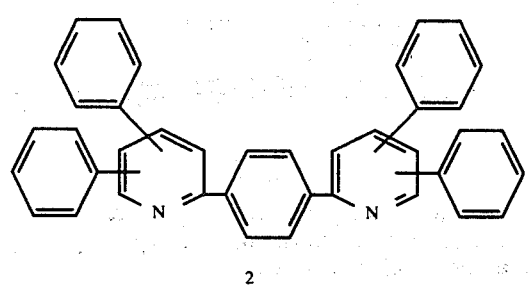

2

EXAMPLE 32

The procedure of Example 31 is followed except that malonic acid dinitrile is used in place of terephthalic acid dinitrile and the mixture is heated for only 5 hours at 85° C.
Charged:
 0.8 g. (3.6 mmoles) methyl heptadienyl-cobalt-butadiene in 50 ml. toluene 6.6 g. (0.1 mole) malonic acid dinitrile 10.2 g. (0.1 mole) phenyl acetylene

| Yield: | 3.9 g. of 1 | (49%) |
| --- | --- | --- |
| | 0.7 g. of 2 | ( 9%) |
| | Total | (58%) |

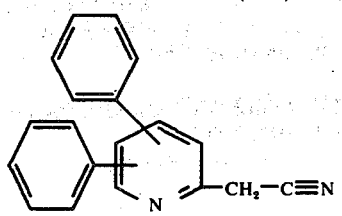

1

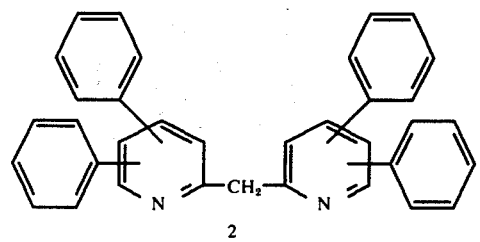

2

EXAMPLE 33

The procedure of Example 31 is followed except that adipic acid dinitrile is used in place of terephthalic acid dinitrile and the mixture is heated for 6 hours at 70° C.
Charged:
 0.6 g. (2.7 mmoles) methyl heptadienyl-cobalt-butadiene in 80 ml. toluene 10.8 g. (0.1 mole) adipic acid dinitrile 10.2 g. (0.1 mole) phenyl acetylene

| Yield: | 5.5 g. of 1 | (55%) |
| --- | --- | --- |
| | 0.9 g. of 2 | (11%) |
| | Total | (66%) |

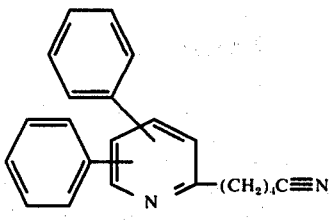

1

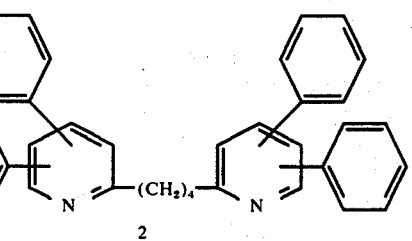

2

EXAMPLE 34

The procedure of Example 31 is followed except that 2-cyano-pyridine is used in place of terephthalic acid dinitrile and the mixture is heated for 5 hours at 60° C.
Charged:
 0.9 g. (4 mmoles) methyl heptadienyl-cobalt-butadiene in 30 ml. toluene
 20.8 g. (0.2 moles) 2-cyanopyridine
 10.2 g. (0.1 mole) phenyl acetylene
Yield:
 2.5 g. of 1 (53%) (mixture of isomers)

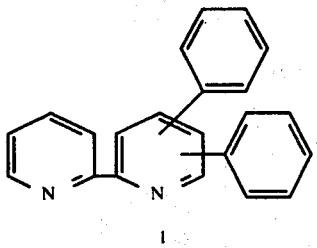

1

EXAMPLE 35

The procedure of Example 31 is followed except that acetonitrile is used in place of terephthalic acid dinitrile and propargyl methyl ether is used in place of phenyl acetylene and the mixture is heated for about 2.5 hours at 60° C.
Charged:
0.5 g. (2.3 mmoles) methyl heptadienyl-cobalt-butadiene in 20 ml. toluene
8.2 g. (0.2 mole) acetonitrile
7.0 g. (0.1 mole) propargyl methyl ether
Yield:
1.7 g. of 1 (68%) (mixture of isomers)

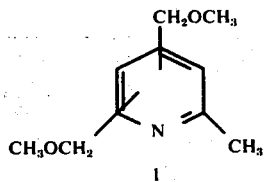

1

EXAMPLE 36

The procedure of Example 31 is followed except that acetonitrile is used in place of terephthalic acid dinitrile and $CH_3$-$CH_2$-C ≡ C-$CH_2$-O-$CH_3$ is substituted for phenyl acetylene and the mixture is heated for about 3 hours at 60° C.
Charged:
3.3 g. (15 mmoles) methyl heptadienyl-cobalt-butadiene in 50 ml. toluene
6.2 g. (150 mmoles) acetonitrile
7.4 g. (75 mmoles) $CH_3$-$CH_2$-C ≡ C-$CH_2$-O-$CH_3$
Yield:
1.7 g. of 1 (61%) (mixture of isomers)

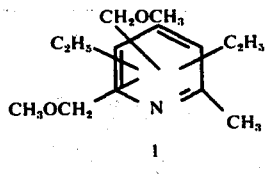

1

EXAMPLE 37

20.5 Grams (500 mmoles) acetonitrile and 20 ml toluene are mixed with 1.0 g. (4.4 moles) cyclopentadienyl-cobalt-cycloocta-(1.5)-diene at room temperature. The resultant brown colored solution is introduced by suction into a 500 ml. stainless steel autoclave. At 20° C, 8 atm. of acetylene are introduced under pressure and the autoclave is heated to 100° C.
resulting in a pressure drop to 5 atm. The pressure is then increased to about 16 atm. while continuously introducing acetylene as it is consumed. After 1.5 hours, the stoichiometrically required amount of 26 g. (1 mole) of acetylene has been taken up. After cooling, the mixture is separated by distillation:

| Fraction 1: | Boiling range 100–111° C./760 torr (benzene and solvent) | 18.0 g. |
|---|---|---|
| Fraction 2: | Boiling point 130° C/760 torr (alpha picoline) | 44.6 g. |
| Residue: | | 1.7 g. |

The fractions 1 and 2 were analyzed by gas chromatography.
Yields based on reacted acetylene: 44.6 g. alpha picoline (96%), 0.8 g. benzene.

EXAMPLE 38

The procedure of Example 37 is followed except that no solvent is used, valeronitrile is substituted for acetonitrile and the reaction is carried out for 2.5 hours at 110°–120° C.
Charged:
0.5 g. (2.2 mmoles) cyclopentadienyl-cobalt-cycloocta-(1,5)-diene
20.8 g. (250 mmoles) valeronitrile
13 g. (500 mmoles) acetylene
The reaction mixture is separated by distillation.

| Fraction 1: | Boiling range 70–185° C./760 torr (first runnings) | 2.0 g. |
|---|---|---|
| Fraction 2: | Boiling point 188° C./760 torr (2-n-butyl pyridine) | 30.7 g. |
| Residue: | | 1.3 g. |
| Yield: | 30.7 g. 2-n-butyl pyridine (91%) | |

EXAMPLE 39

Example 38 is repeated except that caprylonitrile is used in place of valeronitrile and the mixture is allowed to react for 4 hours at 130°.
Charged:
0.7 g. (3.1 mmoles) cyclopentadienyl-cobalt-cycloocta-(1,5)-diene
43.7 g. (350 mmoles) caprylonitrile
18.2 g. (700 mmoles) acetylene
Distillation gives:

| Fraction 1: | Boiling point up to 112° C./13 torr (first runnings) | 2.8 g. |
|---|---|---|
| Fraction 2: | Boiling point 112° C./13 torr (2-n-heptyl pyridine) | 55.1 g. |
| Residue: | | 4.1 g. |
| Yield: | 55.1 g. 2-n-heptyl pyridine (89%) | |

EXAMPLE 40

Example 37 is repeated except that acrylonitrile is used in place of acetonitrile and the mixture is allowed to react for 4 hours at 100° C.
Charged:
0.35 g. (1.5 mmoles) cyclopentadienyl-cobalt-cycloocta-(1,5)-diene
6.65 g. (125 mmoles) acrylonitrile
6.5 g. (250 mmoles) acetylene
50 ml. toluene The reaction mixture is separated by distillation.

| Fraction 1: | Boiling range 20–40° C./13 torr (solvent and first runnings) | 43.8 g. |
| Fraction 2: | Boiling range 50–60° C./13 torr (vinyl pyridine) | 9.8 g. |
| Residue: | | 3.2 g. |
| Yield: | 9.8 g. 2-vinyl pyridine (75%) | |

EXAMPLE 41

Example 37 is repeated except that benzonitrile is used in place of acetonitrile and the reaction mixture is allowed to react for 3 hours at 110°–120° C.
Charged:
- 0.5 g. (2.2 mmoles) cyclopentadienyl-cobalt-cycloocta-(1,5)-diene
- 25.8 g. (250 mmoles) benzonitrile
- 13 g. (500 mmoles) acetylene
- 20 ml. toluene Distillation of the reaction mixture gives:

| Fraction 1: | Boiling range 110° C./760 torr to 120° C./14 torr (solvent and first runnings) | 181. g. |
| Fraction 2: | Boiling point 142° C./14 torr (2-phenyl pyridine) | 36.4 g. |
| Residue: | | 1.2 g. |
| Yield: | 36.4 g. 2-phenyl pyridine (94%) | |

EXAMPLE 42

1.2 g. (5.3 mmoles) cyclopentadienyl-cobalt-cycloocta-(1,5)-diene are dissolved in 20.5 g. (0.5 moles) acetonitrile and 20 ml. toluene and introduced by suction into a 500 ml stainless steel autoclave. At 20° C., 4 atmospheres of propyne are introduced under pressure and the autoclave is heated to 120° C. In doing so, the pressure drops to 2.5 atmospheres. Then the pressure is increased with propyne of 70°–80° C. to about 14 atmospheres so that consumed propyne is continuously supplemented. After 2 hours, the stoichiometrically required amount of 40 g. (1 mole) of propyne has been taken up. Distillation of the reaction mixture gives:

| Fraction 1: | Boiling range 100–111° C./760 torr (solvent) | 17.0 g. |
| Fraction 2: | Boiling range 52–65° C./12 torr (collidine and carbocyclic by-products) | 58.7 g. |
| Residue: | | 2.4 g. |
| Yield: | 39.9 g. 2,4,6-collidine (66%) 16.9 g. 2,3,6-collidine (28%) 1.9 g. pseudocumene and mesitylene | |

EXAMPLE 43

Example 42 is repeated except that propionitrile is used in place of acetonitrile.
Charged:
- 0.5 g. (2.2 mmoles) cyclopentadienyl-cobalt-(cycloocta-(1,5)-diene
- 13.8 g. (250 mmoles) propionitrile
- 20 g. (500 mmoles) propyne and 10 ml. toluene The reaction mixture is separated by distillation.

| Fraction 1: | Boiling range 108–110° C./760 torr (solvent) | 7.9 g. |
| Fraction 2: | Boiling range 58–73° C./12 torr (ethyl pyridines and carbocyclic by products) | 32.3 g. |
| Residue: | | 0.8 g. |
| Yield: | 21.9 g. 2-ethyl-4,6-dimethyl pyridine (65%) 10.4 g. 2-ethyl-3,6-dimethyl pyridine (31%) 0.8 g. pseudocumene and mesitylene | |

EXAMPLE 44

Example 42 is repeated except that benzonitrile is used in place of acetonitrile.
Charged:
- 0.5 g. (2.2 mmoles) cyclopentadienyl-cobalt-cycloocta-(1,5)-diene
- 30.9 g. (300 mmoles) benzonitrile
- 24.0 g. (600 mmoles) propyne and 15 ml. toluene Distillation gives:

| Fraction 1: | Boiling point 110° C./760 torr (solvent) | 12.7 g. |
| Fraction 2: | Boiling range 40–100° C./12 torr (carbocyclic by-products and first runnings) | 4.6 g. |
| Fraction 3: | Boiling range 87–92° C./10$^{-3}$ torr (substituted pyridines) | 48.9 g. |
| Residue: | | 1.4 g. |
| Yield: | 35.7 g. 2-phenyl-4,6-dimethyl pyridine (65%) 13.1 g. 2-phenyl-3,6-dimethyl pyridine (24%) 2.1 g. pseudocumene and mesitylene | |

EXAMPLE 45

Example 42 is repeated except that benzyl cyanide is used in place of acetonitrile.
Charged:
- 0.5 g. (2.2 mmoles) cyclopentadienyl-cobalt-cycloocta-(1,5)-diene
- 28.1 g. (240 mmoles) benzyl cyanide
- 19.2 g. (480 mmoles) propyne and 30 ml. toluene The reaction mixture is separated by distillation.

| Fraction 1: | Boiling point 110° C./760 torr (solvent) | 25.3 g. |
| Fraction 2: | Boiling range 40–120° C./11 torr (carbocyclic by-products and first runnings) | 2.9 g. |
| Fraction 3: | Boiling range 90–100° C./10$^{-4}$ torr (substituted pyridines) | 43.0 g. |
| Residue: | | 1.8 g. |
| Yield: | 30.2 g. 2-benzyl-4,6-dimethyl pyridine (64%) 12.8 g. 2-benzyl-3,6-dimethyl pyridine (27%) 1.6 g. pseudocumene and mesitylene | |

EXAMPLE 46

Example 37 is repeated except that succinic acid dinitrile is used in place of acetonitrile and the mixture is allowed to react for 2 hours at 140° to 150° C.
Charged:
- 0.7 g. (3.1 mmoles) cyclopentadienyl-cobalt-cycloocta-(1,5)-diene
- 20 g. (250 mmoles) succinic acid dinitrile
- 26 g. (1000 mmoles) acetylene and 80 ml. toluene The reaction mixture is separated by distillation.

| Fraction 1: | Boiling range 104–110° C./760 torr (solvent) | 69.6 g. |
| Fraction 2: | Boiling point 124° C./10$^{-3}$ torr | 43.6 g. |
| Residue: | | 1.7 g. |

Yield: 43.6 g. 1,2-di-2-pyridyl ethane (96%)

EXAMPLE 47

Example 37 is repeated except that no solvent is used, azelaic acid dinitrile is used in place of acetonitrile and the mixture is allowed to react for 8 hours at 140–150° C.
Charged:
  0.6 g. (3 mmoles) cyclopentadienyl-cobalt-cycloocta-(1,5)-diene
  37.5 g. (250 mmoles) azelaic acid dinitrile
  26 g. (1000 mmoles) acetylene
Distillation of the reaction mixture gives:

| Fraction 1: | Boiling range up to 120° C./10⁻³ torr (first runnings) | 2.0 g. |
|---|---|---|
| Fraction 2: | Boiling point 138° C./10⁻⁴ torr (1,7-di-2-pyridyl heptane) | 58.4 g. |
| Residue: | | 2.5 g. |
| Yield: | 58.4 g. 1,7-di-2-pyridyl heptane (92%) | |

EXAMPLE 48

Example 37 is repeated except that terephthalic acid dinitrile is used in place of acetonitrile and the mixture is allowed to react for 5 hours at 120–130° C.
Charged:
  0.3 g. (1.3 mmoles) cyclopentadienyl-cobalt-cycloocta-(1.5)-diene
  17.3 g. (125 mmoles) terephthalic acid dinitrile
  13 g. (500 mmoles) acetylene and 30 ml. toluene
The reaction mixture is mixed with 700 ml. toluene and filtered hot (60° C.). After cooling, 250 ml. pentane are added and the product is allowed to crystallize at −80° C.

The product is purified by recrystallization for two times from toluene.
Yield: 27.3 g. p-di-2-pyridyl benzene (94%) (white needles, melting point, 154° C.)

EXAMPLE 49

Example 42 is repeated except that azelaic acid nitrile is used in place of acetonitrile and the mixture is allowed to react for 10 hours at 140°–150° C.
Charged:
  0.5 g. (2.2 mmoles) cyclopentadienyl-cobalt-cycloocta-(1,5)-diene
  25.3 g. (169 mmoles) azelaic acid dinitrile
  27.2 g. (680 mmoles) propyne and 40 ml. toluene
The reaction mixture is separated by distillation:

| Fraction 1: | Boiling point 110° C./760 torr (solvent) | 34.0 g. |
|---|---|---|
| Fraction 2: | Boiling range 20–125° C./10⁻³ torr (first runnings) | 1.1 g. |
| Fraction 3: | Boiling range 158–160° C./10⁻³ torr (dipyridyl heptanes) | 50.8 g. |
| Residue: | | 1.2 g. |
| Yield: | 50.8 g. 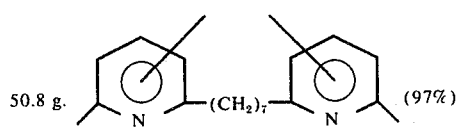 (97%) | |

EXAMPLE 50

Example 37 is repeated except that 2-cyanopyridine is used in place of acetonitrile and the mixture is allowed to react for 10 hours at 120°–130° C.
Charged:
  0.5 g. (2.2 mmoles) cyclopentadienyl-cobalt-cycloocta-(1,5)-diene
  26 g. (250 mmoles) 2-cyanopyridine
  13. g. (500 mmoles) acetylene and 30 ml. toluene
The solvent is separated from the reaction mixture by distillation:
  Fraction 1: Boiling range 108°–111° C./760 torr 25.2 g.
The remaining residue is sublimated:

| Fraction 1: Boiling range 108–111° C./760 torr | 25.2 g. |
|---|---|
| The remaining residue is sublimated: | |
| Fraction 2: Sublimation range 45–55° C./10⁻³ torr | 37.1 g. |
| Residue: | 2.7 g. |
| Yield: 37.1 g. 2,2'-dipyridyl (95%) | |

EXAMPLE 51

Example 37 is repeated except that 3-cyanopyridine is used in place of acetonitrile and the mixture is allowed to react for 5 hours at 120° C.
Charged:
  0.7 g. (3.1 mmoles) cyclopentadienyl-cobalt-cycloocta-(1,5)-diene
  26.0 g. (250 mmoles) 3-cyanopyridine 13 g. (500 mmoles) acetylene
  40 ml toluene
Distillation gives:

| Fraction 1: | Boiling range 106–110° C./760 torr (solvent) | 35.1 g. |
|---|---|---|
| Fraction 2: | Boiling point 92° C./10⁻³ torr (pyrydine) | 35.9 g. |
| Residue: | | 1.9 g. |
| Yield: | 35.9 g. 2,3'-dipyridyl (92%) | |

EXAMPLE 52

Example 42 is repeated except that 3-cyanopyridine is used in place of acetonitrile and the mixture is allowed to react for 7 hours at 120–130° C.
Charged:
  0.5 g. (2.2 mmoles) cyclopentadienyl-cobalt-cycloocta-(1,5)-diene
  20.8 g. (200 mmoles) 3-cyanopyridine
  16.0 g. (400 mmoles) propyne and 35 ml. toluene
Distillation gives:

| | | |
|---|---|---|
| Fraction 1: | Boiling range up to 50° C./13 torr (solvent and by-products) | 30.5 g. |
| Fraction 2: | Boiling range 96–99° C./10$^{-3}$ torr | 33.5 g. |
| Residue: | | 2.4 g. |
| Yield: | 20.6 g. 4,6-dimethyl-2,3'-dipyridyl (56%) 12.9 g. 3,6-dimethyl-2,3'-dipyridyl (35%) | |

EXAMPLE 53

Example 51 is repeated except that 4-cyanopyridine is used in place of 3-cyanopyridine.
Charged:
 0.5 g. (2.2 mmoles) cyclopentadienyl-cobalt-cycloocta-(1,5)-diene
 15.6 g. (150 mmoles) 4-cyanopyridine
 7.8 g. (300 mmoles) acetylene and 25 ml. toluene
The reaction mixture is separated by distillation.

| | | |
|---|---|---|
| Fraction 1: | Boiling range 108–110° C./760 torr (solvent) | 21.5 g. |
| Fraction 2: | Boiling point 97° C./10$^{-3}$ torr | 21.7 g. |
| Residue: | | 2.1 g. |
| Yield: | 21.7 g. 2,4'-dipyridyl (93%) | |

EXAMPLE 54

Examples 52 is repeated except that 4-cyanopyridine is used in place of 3-cyanopyridine.
Charged:
 0.5 g. (2.2 mmoles) cyclopentadienyl-cobalt-cycloocta-(1,5)-diene
 20.8 g. (200 mmoles) 4-cyanopyridine
 16.0 g. (400 mmoles) propyne and 40 ml. toluene
Distillation gives:

| | | |
|---|---|---|
| Fraction 1: | Boiling range up to 55° C./15 torr (solvent and by-products) | 34.8 g. |
| Fraction 2: | Boiling range 120–125° C./10$^{-3}$ torr | 35.3 g. |
| Residue: | | 1.3 g. |
| Yield: | 19.1 g. 4,6-dimethyl-2,4-dipyridyl (52%) 16.2 g. 3,6-dimethyl-2,4-dipyridyl (44%) | |

EXAMPLE 55

Example 37 is repeated except that cyclooctenyl-cobalt-cyclooctadiene is used in place of cyclopentadienyl-cobalt-cycloocta-(1,5)-diene.
Charged:
 0.55 (2.0 mmoles) cyclooctenyl-cobalt-cyclooctadiene
 8.2 g. (200 mmoles) acetonitrile
 10.4 g. (400 mmoles) acetylene
 35 ml. toluene
Distillation as in Example 37 gives:
 15.1 g. 2-picoline (81%)

The foregoing examples are merely illustrative of the practice of the invention. In addition to those catalysts shown, other equivalents may be employed and, where the catalyst is formed by in situ reduction, the salt may be of any inorganic or organic acid, e.g. inorganic acids such as the chloride, sulfate, bromide, nitrate, phosphate, carbonate, and the like, and organic acids such as carboxylic acids, e.g. alkanoic acids, dicarboxylic acids and cyclic acids, and other relatively acidic materials such as phenols, acetylacetone, and the like. The amount of reducing agent should be at least sufficient to reduce cobalt in the requisite amount to form enough catalyst to catalyze the reaction. Advantageously there is enough reducing agent to reduce substantially all of the cobalt, possibly leaving some excess reducing agent. Where the catalyst is preformed, it may be present as a complex with olefins and/or diolefins containing from about 4 to 8 carbon atoms.

The amount of catalyst can be any effective amount, e.g. about 0.1 to 0.01 mole per mole of acetylenic reactant, although greater or lesser amounts are also operative.

For producing pyridines, which contain one ring nitrogen atom and five ring carbon atoms, the acetylenic reactant reacts in twice the molar amount of the nitrile, although either may be present in excess. Often, however, especially when the catalyst is formed in situ, the nitrile is present in large excess, e.g. up to about 4 or more times the stoichiometric amount.

In elaboration of what has been earlier stated, the acetylenic reactant is preferably acetylene, or lower alkyl-, lower alkoxy-, lower alkoxy- lower alkyl- or aryl-substituted acetylenes. The nitrile is preferably a lower alkyl, aryl, aryl-lower alkyl or lower alkenyl nitrile, preferably carrying one or two nitrile groups. In both reactants, the preferred lower alkyl, alkoxy or alkenyl moieties contain up to about 4 carbon atoms and the preferred aryl moiety is phenyl or substituted phenyl.

It will be appreciated that the instant specification and examples are set forth by way of illustration and not limitation, and that various modifications and changes may be made without departing from the spirit and scope of the present invention.

What is claimed is:

1. In the cocyclization of an alkyne selected from the group consisting of acetylene, lower alkyl acetylene, phenyl-acetylene, lower alkoxy-acetylene and lower alkoxy-lower alkyl-acetylene and a nitrile selected from the group consisting of lower alkyl nitrile, phenyl nitrile, phenyl-lower alkyl nitrile and lower alkenyl nitrile in the presence of a cobalt complex compound as catalyst to form a pyridine ring compound, the improvement which comprises employing as said catalyst a member selected from the group consisting of a. a catalyst obtained by reducing a divalent or trivalent cobalt salt in the presence of at least one of the alkyne or nitrile reactants, employing as the reducing agent a metal or organometallic compound wherein the metal is zinc, cadmium or a metal of the main Groups I to III of the Periodic Table of elements, or b. a cobalt-(I) diene complex of the type cyclooctenyl-cobalt(I)-cyclooctadiene, methyl heptadienyl-cobalt(I)-butadiene and cyclopentadienyl-cobalt-(I)-cyclooctadiene.

2. The process of claim 1, wherein the cocyclization is effected at a temperature of about −10° to 150° C.

3. The process of claim 1, wherein the molar amount of the alkyne, an aryl-lower alkyl nitrile and a lower alkenyl nitrile, the catalyst is present in about 0.1 to 0.01 mole per mole of alkyne and the cocyclization is effected at a temperature of about 50° to 100° C.

4. The process of claim 1, wherein said catalyst is obtained by reducing a divalent or trivalent cobalt salt of an organic or inorganic acid in the presence of at least one of the alkyne and nitrile reactants, employing as the reducing agent a metal or organometallic compound wherein the metal is zinc, cadmium or a metal or the main Groups I to III of the Periodic Table of elements.

5. The process of claim 4, wherein the catalyst is obtained at a temperature of about −40° to −10° C.

6. The process of claim 1, wherein the catalyst is at least one member selected from the group consisting of cyclooctenyl-cobalt(I)-cyclooctadiene, methyl heptadienyl-cobalt(I)-butadiene and cyclopentadienyl-cobalt(I)-cyclooctadiene.

7. The process of claim 1, wherein the nitrile is a dinitrile.

* * * * *

UNITED STATES PATENT AND TRADEMARK OFFICE
CERTIFICATE OF CORRECTION

PATENT NO. : 4,006,149　　　　　　　　　　　　　Page 1 of 2
DATED : February 1, 1977
INVENTOR(S) : Helmut Bonnemann et al It is certified that error appears in the above-identified patent and that said Letters Patent are hereby corrected as shown below:

| | |
|---|---|
| Col. 1, line 16 | cancel "Wakasuki" and substitute -- Wakatsuki -- |
| Col. 3, line 8 | cancel "toor" and substitute -- torr -- |
| Col. 3, line 44 | cancel "toor" and substitute -- torr -- |
| Col. 4, line 1 | cancel "toor" and substitute -- torr -- |
| Col. 4, line 8 | cancel "(62% " and substitute -- (62%) -- |
| Col. 5, line 47 | delete "Total (54%)" from the left and place it on the right beneath line |
| Col. 6, line 33 | cancel "uz 25/30" and substitute -- (20%) -- |
| Col. 8, line 60 | after "chlorobenzene" insert new sentence -- The reaction mixture is separated by distillation. -- |
| Col. 8, line 68 | cancel "2,4" and substitute -- 2,5-diphenyl -- |

UNITED STATES PATENT OFFICE
CERTIFICATE OF CORRECTION

Patent No. 4,006,149  Dated Feb. 1, 1977

Inventor(s) Helmut Bonnemann et al.

Page 2 of 2

It is certified that error appears in the above-identified patent and that said Letters Patent are hereby corrected as shown below:

Col. 12, line 28      cancel "toor" and substitute -- torr --.

Col. 17, line 25      Cancel "181" and substitute -- 18.1 --

Col. 12, lines 50-53      lines 50-53 should be between lines 39 and 40

Col. 20, line 47      cancel "toreact" and substitute -- to react --

Col. 22, line 59, claim 3      claim 3 should read as follows:

-- The process of claim 1, wherein the nitrile is present in about 0.5 to 2 times the molar amount of the alkyne, the catalyst is present in about 0.1 to 0.01 mole per mole of alkyne and the co-cyclization is effected at a temperature of about 50 to 100°C. --

Signed and Sealed this thirtieth Day of August 1977

[SEAL]

Attest:

RUTH C. MASON
*Attesting Officer*

C. MARSHALL DANN
*Commissioner of Patents and Trademarks*